(12) United States Patent
Papadimitriou et al.

(10) Patent No.: US 7,231,320 B2
(45) Date of Patent: Jun. 12, 2007

(54) EXTRACTION OF IMPERFECTION FEATURES THROUGH SPECTRAL ANALYSIS

(76) Inventors: Wanda G. Papadimitriou, P.O. Box 801496, Houston, TX (US) 77280; Stylianos Papadimitriou, P.O. Box 801496, Houston, TX (US) 77280

(*) Notice: Subject to any disclaimer, the term of this patent is extended or adjusted under 35 U.S.C. 154(b) by 0 days.

(21) Appl. No.: 11/079,745

(22) Filed: Mar. 14, 2005

(65) Prior Publication Data
US 2006/0111872 A1    May 25, 2006

Related U.S. Application Data

(63) Continuation-in-part of application No. 10/995,692, filed on Nov. 22, 2004, now Pat. No. 7,155,369.

(51) Int. Cl.
*G01B 5/28* (2006.01)
(52) U.S. Cl. ............................ 702/185; 702/34; 702/35; 702/183; 324/228
(58) Field of Classification Search .............. 702/185, 702/13, 6, 9, 1, 17, 33–36, 38–40, 56–59, 702/75–77, 81–84, 79, 113, 183, 184, 189–191, 702/195
See application file for complete search history.

(56) References Cited

U.S. PATENT DOCUMENTS

| | | | |
|---|---|---|---|
| 1,823,810 A | 9/1931 | Wall | 324/241 |
| 2,527,000 A | 10/1950 | Drake | 324/218 |
| 2,582,437 A | 1/1952 | Jezewski et al. | 324/241 |
| 2,685,672 A | 8/1954 | Price et al. | 324/260 |
| 2,770,773 A | 11/1956 | Cooley | 324/221 |
| 2,881,386 A | 4/1959 | Price et al. | 324/225 |
| 3,202,914 A | 8/1965 | Deem et al. | 324/242 |
| 5,321,362 A * | 6/1994 | Fischer et al. | 324/510 |
| 5,371,462 A * | 12/1994 | Hedengren et al. | 324/225 |
| 5,671,155 A | 9/1997 | Edens et al. | 702/38 |
| 5,943,632 A | 8/1999 | Edens et al. | 702/38 |
| 6,115,674 A * | 9/2000 | Brudnoy et al. | 702/38 |
| 6,594,591 B2 * | 7/2003 | Clark et al. | 702/35 |
| 6,727,691 B2 * | 4/2004 | Goldfine et al. | 324/240 |
| 6,784,662 B2 * | 8/2004 | Schlicker et al. | 324/242 |
| 6,975,108 B2 * | 12/2005 | Bilik et al. | 324/237 |
| 2005/0127908 A1 * | 6/2005 | Schlicker et al. | 324/240 |

OTHER PUBLICATIONS

The Inspection of Used Coiled Tubing; Steve Papadimitriou and Roderic K. Stanley; Mar. 28, 1994, 12 pages.

* cited by examiner

*Primary Examiner*—Hal Wachsman
(74) *Attorney, Agent, or Firm*—Kenneth L Nash

(57) ABSTRACT

Autonomous non-destructive inspection equipment provides automatic and/or continuous inspection and evaluation of a material under inspection. The inspection equipment preferably comprises at least one detection sensor and at least one detection sensor interface for a computer. The autonomous non-destructive inspection system may also be retrofitted into conventional inspection systems by extracting pertinent features through spectral frequency analysis and sensor compensation and utilizing those features in the autonomous non-destructive inspection system.

14 Claims, 10 Drawing Sheets

*AutoNDI* Figure 1

*AutoNDI* Figure 2

The minimum GAIN of the PGA is: G = 1 + [R3 / (R2 + R1)]

The maximum GAIN of the PGA is: G = 1 + [R3 / R2]

Example 1:

R1 = 100K          R2 = 5K          R3 = 100K

Maximum GAIN = 21          Minimum GAIN = 1.95

Example 2:

R1 = 100K          R2 = 1K          R3 = 100K

Maximum GAIN = 101          Minimum GAIN = 1.99

---

1st Order Filter

Transfer Function: $H(s) = 1 / (s + \omega_c)$

Design Equation: $R1 = 1 / [2 K \pi C1 F_c] = 1 / [K C1 \omega_c]$

Where:
    Fc = Cutoff Frequency    K, a = Filter Type Constants

---

2nd Order Filter

Transfer Function: $H(s) = 1 / [s^2 + s a \omega_c) = \omega_c 2]$

Design Equations:   $G = 3 - a$ $R2 = 1 / [2 K \pi C2 F_c]$ $R4 = 2 G R2$         $R3 = R4 / [G - 1]$ Where:
    Fc = Cutoff Frequency    K, a = Filter Type Constants

1st Order Filter

Transfer Function: $H(s) = s / (s + \omega_c)$

Design Equation: $R1 = 1 / [2 K \pi\, C1\, F_c] = 1 / [K\, C1\, \omega_c]$

Where:
    $F_c$ = Cutoff Frequency      $K, a$ = Filter Type Constants

2nd Order Filter

Transfer Function: $H(s) = s^2 / [s^2 + s\, a\, \omega_c) = \omega_c^2]$

Design Equations:    $G = 3 - a$ $R2 = 1 / [2 K \pi\, C2\, F_c]$ $R4 = 2\, G\, R2$           $R3 = R4 / [G - 1]$ Where:
    $F_c$ = Cutoff Frequency      $K, a$ = Filter Type Constants

Transforming ANALOG FILTERS to equivalent INFINITE IMPULSE RESPONSE (IIR) DIGITAL FILTERS

Bilinear Transformation is a frequency domain method particularly suited for the design of recursive digital filters, commonly known as IIR Digital filters, by converting an analog filter transfer function H(s) into an equiva -lent digital transfer function H(z).

Each of the Numerator N(s) and Denominator D(s) polynomials is transformed separately by substituting the variable (s) as shown in equation 9.1.

Higher orders of digital filters are obtained by cascading $1^{st}$ and $2^{nd}$ order digital filter.

*FIG. 9A*

The Bilinear Transformation is performed by substituting variables:

$$s = 2 * Fs * \frac{(z-1)}{(z+1)} \quad \text{(Eq. 9.1)}$$

where Fs is the Sampling Frequency

*FIG. 9B*

The frequency response of the IIR Digital filter is obtained by substituting:

$$z = e^{j\omega/Fs} \quad \text{(Eq. 9.2)}$$

*FIG. 9C*

A typical analog filter transfer function is of the form:

$$H(s) = \frac{\sum_{i=0}^{m} a_i s^i}{\sum_{i=0}^{n} b_i s^i} = \frac{N(s)}{D(s)} \quad \text{(Eq. 9.3)}$$

where m is less or equal to n

*FIG. 9D*

WAVELETS

For discrete time samples, the wavelet transform can be accomplished by applying filter banks. A typical decomposition filter bank is shown below.

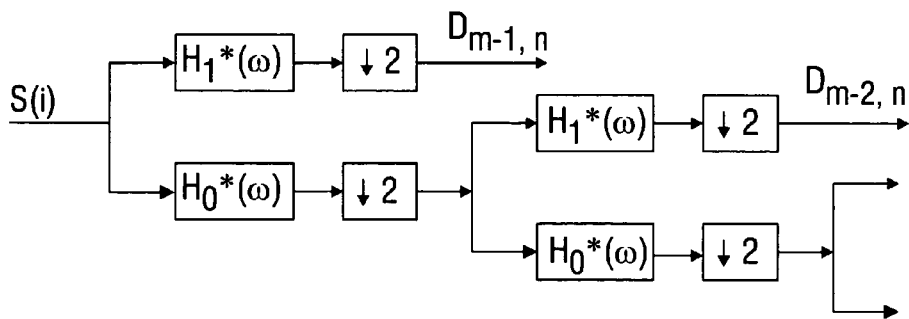

Where S(i) is the original signal; $D_{m,n}$ are wavelet series coefficients and ↓ denotes downsampling by 2.

*FIG. 10A*

The HAAR wavelet $$H_0(\omega) = 0.5(1 + e^{-j\omega})$$

describes a low-pass filter where Ho(0) = 1 and Ho(π) = 0

*FIG. 10B*

The quadrature mirror filter of Ho(ω) is H₁(ω)

$$H_1(\omega) = 0.5(1 - e^{-j\omega})$$

a high-pass filter.

*FIG. 10C*

EXTRACTION OF IMPERFECTION FEATURES THROUGH SPECTRAL ANALYSIS

RELATED APPLICATION

This application is a continuation in part of U.S. patent application Ser. No. 10/995,692 having a filing date of Nov. 22, 2004, having been published on May 25, 2006 as Publication No.: US2006/0111872 A1 and now U.S. Pat. No. 7,155,369.

TECHNICAL FIELD

This invention relates, generally, to non-destructive inspection and inspection equipment, and more specifically, to provide implementation of automatic and/or continuous non-destructive inspection and evaluation for inspection equipment of material under inspection, including evaluators and predictors of detected imperfections and useful material life.

BACKGROUND OF THE INVENTION

As is known in the art, materials are selected for use based on criteria including minimum strength requirements, useable life, and anticipated normal wear. Safety factors are typically factored into design considerations to supplement material selection in order to aid in reducing the risk of failures including catastrophic failure. Such failures may occur when the required application strengths exceed the actual material strength. During its life, the material is weakened by external events such as mechanical and/or chemical actions arising from the type of application, repeated usage, hurricanes, earthquakes, storage, transportation, and the like; thus, raising safety, operational, functionality, and serviceability issues throughout the materials life. Non-Destructive Inspection (herein after referred to as "NDI") is carried out, at least in part, in order to verify that the material exceeds the minimum strength requirements for the application.

Since its inception in the early 1900s, the NDI industry has utilized a variety of techniques and devices with the majority based on the well known and well documented techniques of magnetic flux leakage (herein after referred to as "MFL"), magnetic particle, eddy-current, ultrasonic, radiation, such as x-ray and gamma ray, dye penetrant, and dimensional as well as visual and audible techniques. These techniques have been utilized alone or in combination with each other to address the specifics of the Material-Under-Inspection (herein after referred to as "MUI"). A list of typical MUI includes, but is not limited to, engine components, rails, rolling stoke, oil country tubular goods (herein after referred to as "OCTG"), chemical plant components, pipelines, bridges, structures, frames, cranes, aircraft, sea going vessels, drilling rigs, workover rigs, vessels, structures, other components of the above, combinations of the above, and similar items.

A prolifically used MFL inspection unit is found in U.S. Pat. No. 2,685,672 and in particular, the sensors and their arrangement as described in FIGS. 5 and 6 are still in use today with hundreds of units employed worldwide in portable or stationary configurations. The same sensor configuration is also described in FIG. 7 of U.S. Pat. No. 2,881,386. This type of NDI is commonly referred to as Electro Magnetic Inspection (herein after referred to as "EMI"). These types of units utilize a magnetizing coil to induce a magnetic field into the MUI. It should be understood that the magnetic field can be applied in any direction. U.S. Pat. No. 2,685,672 shows the induction of a longitudinal magnetic field while U.S. Pat. No. 3,202,914 shows the induction of a transverse magnetic field.

Since these types of EMI units deploy a single sensor per area of MUI, they are classified as one-dimensional (herein after referred to as "1D")units. In this type of EMI unit, the signal of each 1D sensor is typically amplified and filtered by a high-pass filter for system stability and by a low-pass filter to remove the noise. Referring to FIG. 6 of U.S. Pat. No. 3,202,914, capacitor 51 and its associated components form a high-pass filter while capacitor 48 and its associated components form a low-pass filter. The highest signal is then selected for presentation to the inspector under an assumption, now widely accepted as being false, that the highest signal corresponds to the worst imperfection. EMI units with multichannel chart recorders assign sensors to a group and then they select the highest signal within the group for presentation to the inspector.

The main drawback of these EMI units is that they are one-dimensional and specifically, that the signal of any 1D sensor can be used as a variable to only one equation. Centuries of strength-of-material knowledge however, define NDI as a multidimensional problem that can never be solved in 1D. The severity of any imperfection, its failure-potential, is a function of its overall geometry, its immediate neighborhood and the loads applied to the MUI, but it is never a function of its response to magnetic excitation. In fact, large 1D signals often arise from well known material features such as braces, tapers, etc. while the detection of dangerous defects, such as fissures or cracks, is the aim of NDI. This predicament, further discussed below, is also illustrated in U.S. Pat. No. 2,527,000.

It is therefore desirable to retrofit Autonomous NDI (herein after referred to as "AutoNDI") capabilities to the hundreds of 1D EMI units deployed worldwide. The imperfection features discussed in the AutoNDI prior U.S. application Ser. No. 10/995,692 are derived by the extraction matrix. The extraction matrix however, cannot solve a multidimensional problem with only one variable. This problem can be solved by compensating and then analyzing in detail the frequency spectrum of the imperfections to derive a frequency based flaw spectrum for further use by the AutoNDI.

Early on, NDI recognized that the inspection sensor signals were made-up from components of different frequencies. It was readily apparent that the lower frequency components originated from material features that were large while smaller material features gave rise to the higher frequency components. Most of the large material features were often designed into the MUI, thus these features were known in advance, or they could be observed visually while the smaller features were mostly associated with imperfections and could not readily be observed visually.

This often encountered NDI predicament is addressed in the first paragraph U.S. Pat. No. 2,527,000 and it is also shown graphically in its FIG. 3. While searching for small imperfections " . . . to discover any irregularities caused by the presence of fissures or other discontinuities in the rail . . . " the large MUI features that were part of the original rail design " . . . rails are joint by angle-bars, bolts . . . which constitute in themselves irregularities . . . " interfere with the detection of the fissures "As a result, should an internal fissure occur in the rail within the region of the angle bar or closely adjacent to the ends of the angle bar it would be impossible to distinguish such fissure from any other indication". The oil country tubular goods (OCTG) NDI face a similar problem with pipe collars (couplings) and the detection of small imperfections on or in the vicinity of the collars, which has typically been assigned to an offline manual inspection/verification crew. For example, during a trip, when tubing or drill pipe is pulled out of a well, every singlejoint must be broken off the stand and laid down separately instead of standing up double or triple stands. This process creates a very expensive, labor intensive, and time consuming endeavor. Therefore, it is desired in the art, to provide a simple solution to this predicament by deploying the AutoNDI features.

Early NDI units focused on the smaller imperfections by passing the inspection sensor signal through a high-pass frequency filter and thus selecting its higher frequency components for presentation to the inspector. A high-pass filter is also known in the art as Low-Reject, Low-Cut, DC-block, or AC-Coupler. The simplest high-pass filter known to the art is made up by a capacitor followed by a resistor and can be found in patents such as U.S. Pat. No. 2,582,437 (see FIG. 1 capacitor 13 and resistor 40). Two such filters can be seen in the earlier U.S. Pat. No. 1,823,810 (see FIG. 1, amplifier 20) as well as in U.S. Pat. No. 5,671,155 (see FIG. 1, AC-couplers 6) and U.S. Pat. No. 5,943,632 (see FIG. 1, AC-couplers 6).

U.S. Pat. No. 2,770,773 encompasses many elements of the above to detect corrosion pitting and clearly states a frequency separation essential element, the frequency versus scanning speed interdependence. The high-pass filters of FIG. 7 (capacitors 66, 67 and resistors 69, 70) remove many unwanted " . . . signal producing variables such as separation from the casing wall, wall roughness, misfit . . . " [Column 6, Line 15]. Following the high-pass filter is a band-pass filter ". . . to pass frequencies in the band between about 3 and 20 cycles per second, as this is the characteristic frequency range of signal due to the passage of the shoe 15 across a casing corrosion pit at a transverse speed of twenty feet per minute. This frequency band related to the speed of traverse of the instrument 10 through the casing 12 will, of course, be varied to suit any other traverse speed selected" [Column 6, Line 33]. It is well known in the NDI art that the frequency range of the imperfection signal is proportionately related to the scanning speed. Thus the frequency range of the filters must be adjusted for different scanning speeds, an essential element missing from U.S. Pat. Nos. 5,671,155 and 5,943,632. Thus, it is desired, in the art, to provide a simple compensation technique to fulfill this essential element. Such a compensation technique is further described herein below.

Yet another example of this technology can be found in U.S. Pat. No. 3,202,914. The MFL signal for different types of imperfections is shown in its FIG. 5. The specification is written in terms of time which is inversely proportional to frequency and it utilizes both frequency filtering and purpose built sensors to separately process the imperfection signals. This is found at Column 5, Line 57 "Signals from the rod wear search coils 8 and 9, being of low level and low frequency . . . " and at Column 6, Line 37 "Thus the values of resistance 50 and Capacitor 51 are chosen so that the high frequencies of the signals from the seam pass . . . ", a classical separation of rod wear and seam signals. For the same sensor and scanning speed, rod wear, being wider than a seam by at least an order of magnitude, gives rise to lower frequency signal than the seam. Examples of this technology are inspection units offered by OEM, Inc. San Antonio, Tex.

Another early observation of the NDI industry is the scanning speed versus signal amplitude proportional interdependence for coil sensors. U.S. Pat. No. 2,881,386 (see FIGS. 10 and 11) provides a technique for amplitude compensation for the scanning speed variations.

There are many drawbacks associated with this signal processing technology. In nature, even simple imperfections are made up of multifaceted slopes, each slope giving rise to signals of different frequency. Thus, there is no single frequency component exclusively associated with any imperfection type. U.S. Pat. No. 2,770,773 associates the frequency band of 3 Hz to 20 Hz primarily with corrosion pitting signals at the scanning speed of 20 ft/min. However, other imperfections, such as the ends of wall thickness changes could also give rise to signals with frequency components within the same frequency band. The above shortfalls, of conventional inspection equipment, explain the NDI industry's extensive use of manual verification whereby the inspection unit flags an area on the MUI and the verification crew investigates further using visual, dye penetrant, mag particle, ultrasonic, x-ray, pressure testing, and/or miscellaneous other manual techniques. Manual verification is typically performed offline, utilizes specialty inspection equipment and inspectors skilled in a multitude of inspection techniques, it is time consuming, and is therefore very expensive.

Furthermore, imperfections in nature coexist and when detected give rise to even more complex waveforms that include a multitude of frequency components including their sums and differences. This often occurs in materials that endure dynamic loading, where simple corrosion pits become stress concentrators resulting in cracks forming at the bottom of the corrosion pits. The prior art does not address this complexity.

Another drawback of the conventional inspection systems, is the scanning speed interdependence of the imperfection signal frequency spectrum, discussed in U.S. Pat. No. 2,770,773, which prohibits the use of frequency filters with fixed characteristics such as the ones used in U.S. Pat. Nos. 5,671,155 and 5,943,632.

BRIEF DESCRIPTION OF THE DRAWINGS

FIG. 9A illustrates the Bilinear Transformation, a mathematical technique to translate an analog transfer function to the digital domain, according to the present invention;

FIG. 9B illustrates a mathematical formula for the Bilinear Transformation illustrated in FIG. 9A according to the present invention;

FIG. 9C illustrates a mathematical formula for an IIR Digital filter for the Bilinear Transformation illustrated in FIG. 9A according to the present invention;

FIG. 9D illustrates a mathematical formula for an analog filter transfer function for the Bilinear Transformation illustrated in FIG. 9A according to the present invention;

FIG. 10A illustrates the block-diagram to implement the discrete wavelet transform decomposition through digital filter banks according to the present invention.

FIG. 10B illustrates a mathematical formula for a lowpass filter of a HAAR wavelet of FIG. 10A according to the present invention; and FIG. 10C illustrates a mathematical formula for a highpass filter of a HAAR wavelet of FIG. 10A according to the present invention.

DETAILED DESCRIPTION OF EMBODIMENTS OF THE INVENTION

To understand the terms associated with the present invention, the following descriptions are set out herein below. It should be appreciated that mere changes in terminology cannot render such terms as being outside the scope of the present invention.

Autonomous: able to function without external control or intervention.

Classification: assigning an imperfection to a particular class based on its features.

Decomposed in Frequency: Separating desirable characteristics from a frequency response gathered during an inspection process.

Defect: an imperfection that exceeds a specified threshold and may warrant rejection of the material under inspection.

Flaw Spectrum: A presentation of data derived from a multidimensional sensor utilizing an extraction matrix.

Frequency Based Flaw Spectrum: A presentation of data derived from a 1D sensor in combination with filter banks to decompose and interpret the sensor received information.

Imperfection Or Flaw: a discontinuity, irregularity, anomaly, inhomogenity, or a rupture in the material under inspection.

Knowledge: a collection of facts and rules capturing the knowledge of one or more specialist.

Normalization: Amplitude, and/or phase, and/or bandwidth, and/or time shifting adjustments of the inspection sensor output to compensate for the system implementation idiosyncracies that affect the inspection sensor output such as changes/differences due to scanning speed and/or implementation geometry and/or excitation and/or for response characteristics of the inspection sensor.

Response Characteristics: Desirable characteristics separated from a frequency response to be evaluated preferably by a computer to determine imperfections.

Rules: how something should be done to implement the facts.

Scanning Speed: The speed of the MUI passing the sensor (or the speed of the sensor along the MUI).

Figure 1:
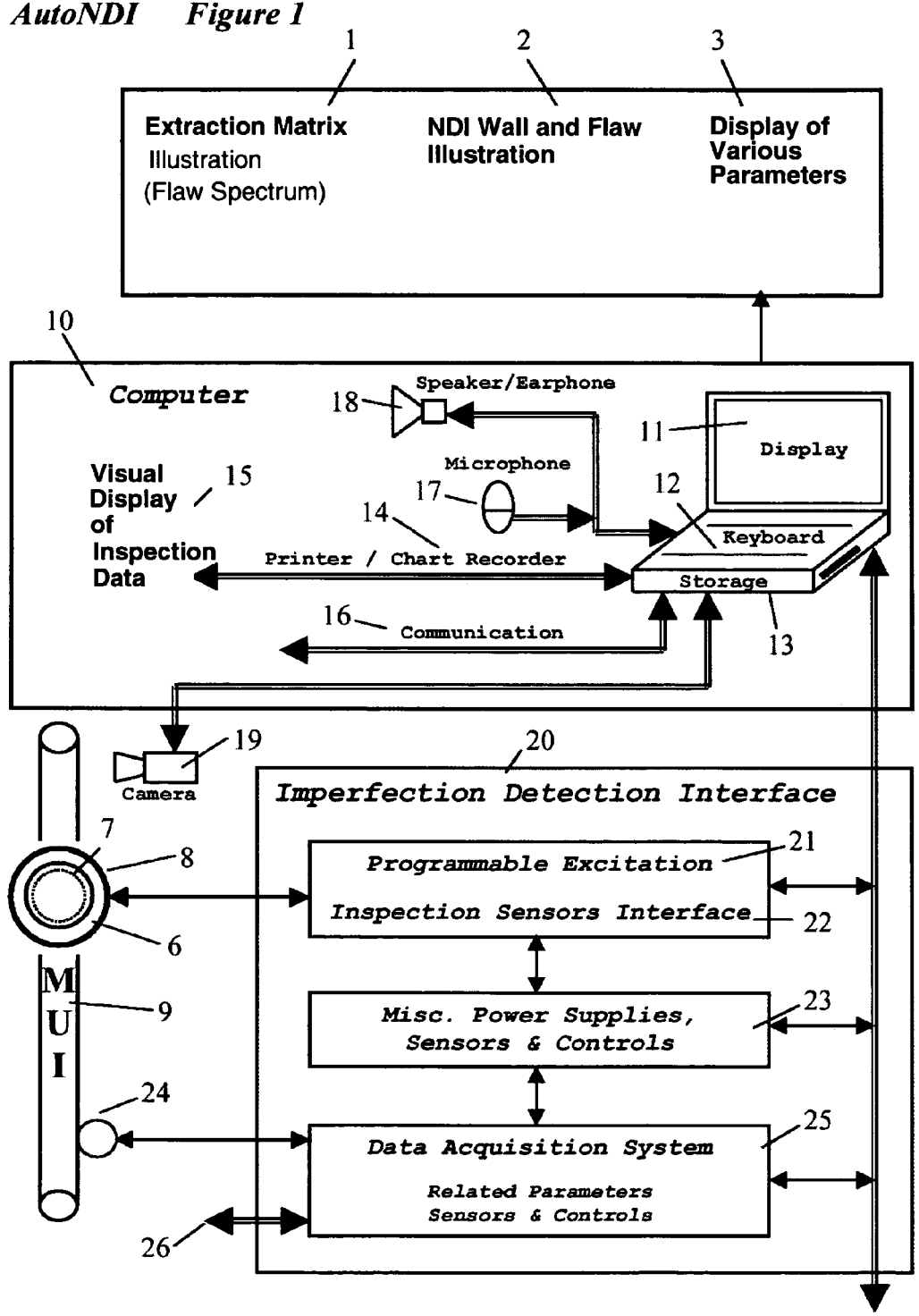
FIG. 1 illustrates a block diagram of an autonomous non-destructive inspection system according to the present invention.

FIG. 1 illustrates a block diagram of an inspection system further illustrating the inspection computer 10, the imperfection detection interface 20, and the preferable information exchange among the components of the inspection equipment. It should be understood that the inspection computer 10 may include more than just one computer such as a cluster of interconnected computers. It should be understood that the computer 10 does not necessarily comprise a laptop or portable personal computer and such misinterpretation should not be made from the illustrations in the figures and shall not be read as a limitation herein. The computer 10 preferably comprises a keyboard 12, display 11, storage capacity 13, for storing and accessing data, a microphone 17, a speaker 18 and a camera 19. It should be understood that the display 11, the keyboard 12, the microphone 17 and the speaker 18 may be local to the computer 10, may be remote, may be portable, or any combination thereof. It should be further understood that camera 19 may comprise more than one camera. Further camera 19 may utilize visible light, infrared light, any other spectrum component, or any combination thereof. The camera 19 may be used to relay an image or a measurement such as a temperature measurement, a dimensional measurement, a comparative measurement, or any combination thereof including information to identify the MUI. It should be appreciated that the stored data may comprise hard disks, floppy disks, compact discs, magnetic tapes, DVDs, memory, and other storage devices. The computer may transmit and receive data through at least one communication link 16 and may send data to a printer or chart recorder 14 for further visual confirmation of the inspection data 15 and other related information. The computer 10 preferably provides for data exchange with the imperfection detection interface 20.

NDI dictates termination of the material utilization altogether in order to accommodate the inspection process, which, is typically carried out by shipping the material to an inspection facility. The cost of inspection is therefore increased by the transportation cost and the material downtime. In addition, shipping and handling the material, especially after the inspection, may induce damage to the material that could result in an unanticipated early catastrophic failure.

Because of its implementation and the intrusion NDI imposes, typical inspections have been expensive and were thus performed at rare intervals or not performed at all. For example, NDI costs of OCTG can be as high as 30% of the material replacement cost. The novel autonomous inspection system, control, and method that is presented hereinbelow can be used as an "advisor" to an inspector or as a stand alone low-cost inspection system. It should be appreciated that as an "advisor" the system can be used in conjunction with typical or conventional inspection systems at the typical intervals such conventional systems are used.

As a stand alone system, the autonomous inspection system can bring the cost of inspection down due to its non-intrusive implementation and on-going inspection. The non-intrusiveness allows for the inspection to be carried out, in many applications, while the MUI 9 is in operation and without requiring the operation to stop (such as, but not limited to, when running OCTG into or out of a well or evaluating/inspecting refinery or chemical plant piping while in use). Further, because of the nature of the constant inspection, major defects are more likely to be found and minor defects can be better monitored over time to predict the useable life the MUI 9. It is well known that the presence of any imperfection alters the expected (designed) life-cycle of the MUI 9 and thus impacts its remaining useful life. Thus, it should be appreciated that the autonomous inspection system and method would increase safety and reliability as useful life predictors would be more accurate and lead to MUI 9 repair/replacement prior to catastrophic failures of the MUI 9 as well as premature replacement due to concerns when the conventional inspection periods are spaced far apart.

The Autonomous Non-Destructive Inspection (AutoNDI) detects and classifies imperfections without altering the MUI 9 using mostly indirect techniques. Pipe for example, is manufactured based on metallurgy, geometry, strength, and other parameters. The pipe's response to magnetic or ultrasonic excitation is not one of the design criteria. MFL based NDI, attempts to detect imperfections using magnetism. However, the response of an imperfection to a magnetic field is not directly related to its effect on the strength of the MUI, preferably the ultimate inspection goal. Secondly, its response to a magnetic field is partially controlled by its previous magnetic state. Thus, with most conventional inspection systems MFL based NDI has been used as a flag for a verification crew. The inspector monitors the magnetic flux leakage traces and instructs the verification crew to investigate a particular indication (possible defect). Thus, with most conventional inspection systems, the MUI owners or operators typically specify that the verification crew investigate at least ±six inches on either side of an indication. It is also not uncommon for the inspector to recognize certain imperfections from the chart, given enough experience.

A common way to reduce verification time (which translates to cost) is to assume that all the imperfections are of a certain type and are all located on a specific surface of the material. Then, the signal amplitude and/or width can be used as a pass/fail indicator. Typically, such a process has very limited application specific success.

Regardless of the specific inspection technique utilized, the autonomous NDI device will preferably scan the material after each use, fuse the inspection data with relevant material use parameters, and automatically determine the MUI 9 status. Thus, a function of the imperfection detection interface 20 is to generate and induce excitation 21 into the MUI 9 and detect the response, of the MUI 9, to the excitation 21. Preferably, at least one inspection head 8 is mounted on or inserted in the MUI 9 and the head 8 may be stationary or travel along the MUI 9. It should be appreciated that the inspection head 8 can be applied to the inside as well as the outside of the MUI 9. It should be understood that the inspection head 8, illustrated herein, may comprise at least one excitation inducer 6 and one or more inspection sensors 7 mounted such that the inspection needs of MUI 9 are substantially covered. For MFL inspection, the excitation inducer 6 typically comprises of at least one magnetizing coil and/or at least one permanent magnet while sensor 7 comprises of sensors that respond to magnetic field. There is a plethora of sensors that respond to the magnetic field such as coils, Hall-probes, magneto diodes, etc. The inspection computer 10 preferably both programs and controls the excitation 21 and the inspection head 8 as well as receives data from the inspection head sensors 7 through the inspection sensor interface 22. The inspection head 8, excitation 21, and the inspection sensor interface 22 may be combined within the same physical housing. In an alternative embodiment, the inspection sensors 7 may comprise at least one computer and/or processor and memory storage and thus the sensors 7 can be programmed to perform many of the tasks of the computer 10 or perform functions in tandem with the computer 10. It should be also understood that the application of the excitation 21 and the inspection of the MUI 9 may be delayed such as NDI utilizing far-field or the residual magnetic field whereby the MUI 9 is magnetized and it is inspected at a later time, thus the excitation inducer 6 and the inspection sensor 7 may be mounted in different physical housings. It should be further understood, that in such configuration, the excitation inducer 6 may be applied on the inside or on the outside of MUI 9 while the inspection sensor 7 may be applied on the same side or on the opposite side of the excitation inducer 6. It should be further understood that either or both the excitation inducer 6 and the inspection sensor 7 may be applied on both the inside and on the outside of MUI 9 so that the inspection needs of MUI 9 are substantially covered.

Computer 10 also controls and monitors a plurality of power supplies, sensors and controls 23 that facilitate the inspection process including but not limited to MUI 9 identification and safety features. Further, computer 10 monitors/controls the data acquisition system 25 which preferably assimilates data from at least one sensor 24. The sensor 24 preferably provides data such as, but not limited to, MUI 9 location (feet of MUI 9 passing through the inspection head 8), penetration rate (speed of MUI 9 moving through the inspection head 8), rate of rotation (rpm), and coupling torque. It should be appreciated that the data to be acquired will vary with the specific type of MUI 9 and thus the same parameters are not always measured/detected. For example, the length of the MUI 9, such as a drill pipe joint, may be read from the MUI 9 identification markings or from the identification tag embedded in the MUI 9. Furthermore and in addition to the aforementioned inspection techniques, computer 10 may also monitor, through the data acquisition system 25, parameters that are related to the inspection or utilization of the MUI 9. Such parameters may include, but not be limited to, the MUI 9 internal pressure, external pressure, such as the wellhead pressure, temperature, flow rate, tension, weight, load distribution, and the like. Preferably, these parameters are measured or acquired through sensors and/or transducers mounted throughout the inspection area, such as a rig. For ease of understanding, these various sensors and transducers are designated with the numeral 26. The STYLWAN Rig Data Integration System (RDIS-10) is an example of such an inspection system (STYLWAN is a trademark of Stylwan, Incorporated). It should be appreciated that the RDIS-10, is a hybrid system combining inspection and data acquisition, uses the extraction matrix to inspect, not the frequency based flaw spectrum and that the extraction matrix works with multidimensional sensors, not with frequency spectrums. When however, the multidimensional sensors and extraction matrix are replaced with a different sensor interface and a bank of frequency filters, the RDIS-10, a hybrid system combining inspection and data acquisition, will work as described herein utilizing the frequency derived flaw spectrum.

Preferably, the inspection head 8 relates time-varying continuous (analog) signals, such as, but not limited to, echo, reluctance, resistance, impedance, absorption, attenuation, or physical parameters that may or may not represent an imperfection of the MUI 9. For MFL inspection, inspection head 8 relates reluctance signals in an analog form. The processing of Eddy-Current amplitude and phase would also result in similar analog signal. It should be appreciated, by those in the art, that sensor 7 signals generally include, but are not limited to, noise and useable data that may indicate some imperfection and/or defect. Further, imperfections generally comprise all received signals and may include MUI 9 design features such as tapers, major and minor defects or other MUI 9 conditions such as surface roughness, hardness changes, composition changes, scale, dirt, and the like. Still further, defects may be viewed as an imperfection of a specific magnitude or beyond a certain threshold. Typically, those in the art have always relied on both an inspector and a manual verification crew for the interpretation of the inspection signals and any subsequent disposition of the MUI 9. However, based on extensive strength-of-materials knowledge, it is well known that the severity of an MUI 9 imperfection is a function of its geometry, its location, and the applied loads. It is also well known, in the art, that this information cannot be readily obtained by a verification crew when the imperfections in question are located underneath coating, in the near subsurface, in the mid wall, or in the internal surface of the MUI 9. Any destructive action, such as removing any coating or cutting up the MUI 9 is beyond the scope of non-destructive inspection. Detailed signal analysis can extract the pertinent information from the NDI signals. Preferably, such detailed signal analysis would utilize signals that are continuously related in form, kind, space, and time. The analog signals from inspection head 8 are preferably band limited and are then decomposed in frequency. This frequency decomposition can take place in continuous or discrete form. In the continuous form the signals are decomposed through a bank of analog frequency filters and they are then digitized by the computer 10. In the discrete form the signals are digitized by the computer 10 and they are then decomposed through a bank of digital frequency filters or mathematical transforms. Regardless of the frequency decomposition method used, the frequency components of the signals then become the flaw spectrum for use by the AutoNDI in a manner illustrated by element 1 in FIG. 1. It should be understood that computer 10 can manipulate and present the signals in any desirable format. It should be further understood that the signals of geometrically offset sensors, such as the ones shown in FIG. 7 of U.S. Pat. No. 2,881,386, are aligned by computer 10 through time shifting (also known as time delay) primarily controlled by the scanning speed. This may comprise memory, a bucket-brigade, or any combination of the above. Variable length analog delay lines may also be deployed, the delay length controlled primarily by the scanning speed.

It should be understood that the extraction matrix is compiled through a software program, that was published in 1994 and it is beyond the scope of this patent, and decomposes the converted digital signals into relevant features. The extraction matrix may be adjusted to decompose the signals into as few as two (2) features, such as, but not limited to, the classical NDI presentation of wall and flaw in a manner illustrated by element 2 in FIG. 1. It should be understood that no theoretical decomposition upper limit exists, however, fifty (50) to two hundred (200) features are practical. The selection of the identifier equations, further described herein below, typically sets the number of features. In the exemplary RDIS-10, a hybrid system combining inspection and data acquisition, the decomposed signals are known as the flaw spectrum 1 (see element 1, FIG. 1).

Humans are highly adept in recognizing patterns, such as facial features or the flaw spectrum 1 and readily correlating any pertinent information. Therefore, it is easy for the inspector to draw conclusions about the MUI 9 by examining the flaw spectrum 1. During the inspection, the inspector further incorporates his/her knowledge about the MUI 9 present status, his/her observations, as well as the results of previous inspections. The success of this inspection strategy of course, solely depends on how well the inspector understands the flaw spectrum 1 data and the nuances it may encompass.

Computers can run numerical calculations rapidly but have no inherent pattern recognition or correlation abilities. Thus, a program has been developed that preferably derives at least one mathematical procedure to enable the computer 10 to automatically recognize the patterns and nuances encompassed in decomposed inspection data streams such as presented in the flaw spectrum 1. The detailed mathematical procedures are described hereinbelow and enable one skilled in the art to implement the autonomous NDI described herein without undue experimentation.

Figure 2:
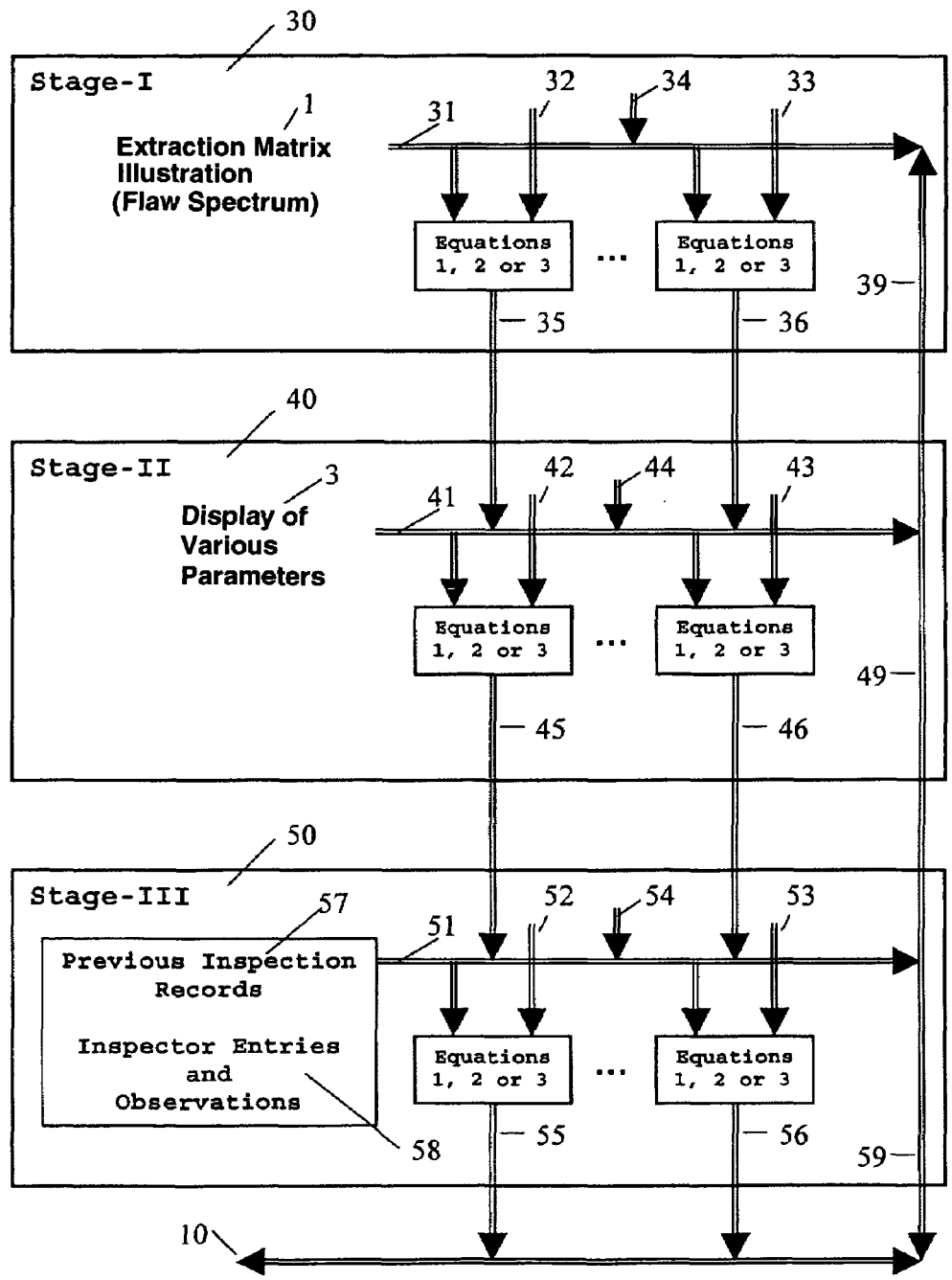
FIG. 2 illustrates a block diagram of the signal processing of an autonomous non-destructive inspection system according to the present invention.

FIG. 2 illustrates a block diagram of an inspection data processing sequence that allows the creation of a software flowchart and the translation of the practice to a computer program. For stand-alone operation, the autonomous NDI must be optimal in regard to the inspection criteria and application limitations, commonly defined by approximations and probabilities which are referred to herein as constrains. It should be understood therefore, that the autonomous NDI state variables must be tuned for optimal performance under different constrains depending on the MUI 9 and its application. The fundamental operation of the autonomous NDI is performed by the identifier equations which preferably capture the optimal mutual features in accordance to the constrains. It should be understood that a number of identifier equations may be paralleled and/or cascaded, each one utilizing a different set of optimal mutual features. Furthermore, it should be understood that the processing of the identifier equations may be carried out by a single computer 10 or by different computers in a cluster without effecting the overall result.

The first stage identifier equations, with elements denoted as $a_{jk}$ 32, 33, use for input N features 31 mostly derived from the flaw spectrum 1. Additional features may be provided by fixed values referred to herein as bias 34, 44, 54. Bias may be a single constant or a sequence of constants that may be controlled, but not limited, by time or by the MUI 9 length. Backwards chaining 39 limits irrelevant processing and enhances stability while forward chaining 59 propagates features to later stages or it may inform computer 10 that an MUI 9 condition has been determined and no further analysis is required. It should be further understood that both forward and backward chaining may be direct, through memory, through a bucket-brigade, or any combination of the above. It should be further understood that all or any subsystem of the autonomous NDI may be implemented as a casual system or as a non-casual system. In a casual implementation only past and present features 31 are utilized. In a non-casual implementation, features 31 are utilized through memory, through a bucket-brigade, or any combination of the above thus allowing for the use of future values of the features 31. Future values of the features 31 may be used directly or indirectly as signal masks and may be propagated through the forward chaining 59. Utilization of future values of features 31 increases the AutoNDI stability and reduces the probability of a conflict In Equations 1–3, shown below, such features are denoted as Xa. Based on the constrains, the identifier equations reduce the features 31 and bias 34 to identifiers 35, 36 denoted as Ya of the form:

$$Ya_{ij} = M \sum_{k=1}^{N} a_{ik} Xa_{kj} \qquad \text{(Equation 1)}$$

The identifiers Ya 35, 36 can be fed back through the backwards chaining 39, can be used directly through the forward chaining 59, can be used as variables to equations or as features 41, 51 in following stages or in their most practical form, as indexes to tables (arrays) which is shown in Equation 2 for clarity.

$$Ya_{ij} = T_{\left(M \sum_{k=1}^{N} a_{ik} Xa_{kj}\right)} \qquad \text{(Equation 2)}$$

where T is a Look-up Table or Array.

Another useful identifier form is shown in Equation 3.

$$Ya_{ij} = M \left[1 + e^{-\sum_{k=1}^{N} a_{ik} Xa_{kj}}\right]^{-1} \qquad \text{(Equation 3)}$$

where M is a scaling constant or function.

It should be understood that each stage may comprise multiple identifier equations utilizing equations 1, 2, or 3. There is no theoretical upper limit for the number of identifiers calculated, however, five (5) to ten (10) identifiers are practical.

Some of the identifiers Ya 35, 36 may be sufficient to define the disposition of the MUI 9 alone and thus propagate to the output stage 59 while others may become features for the second stage 40 of identifier equations along with features 41 pertinent to the Ya identifiers, all denoted as Xb. It should be appreciated that in the exemplary STYLWAN RDIS-10, a hybrid system combining inspection and data acquisition, depending on the constrains, those features can be obtained from the operator interface, from the computer 10 memory, from the camera 19, or by connecting directly to the STYLWAN RDIS-10 Data Acquisition System transmitters that measure various parameters illustrated FIG. 1 (3) (STYLWAN is a trademark of Stylwan, Incorporated). Examples of such transmitters include the OAI-5000 series manufactured by OLYMPIC CONTROLS, mc, Stafford, TX, USA, such as transmitters that measure pressure (OAI-5200 series), temperature (OAI-5300 series), speed and position (OAI-5400 series), weight (OAI-5200H series), fluid level (OAI-5200L series), flow (OAI-5600 series), dimensions (OAI-5400D series), AC parameters (OAI-5400 series), DC parameters (OAI-5800 series), as well as other desired parameters (OAI is a trademark of Olympic Controls, Incorporated). The second stage 40 identifier equations, with elements denoted as $b_{lm}$, produces identifiers 45,46 denoted as Yb of similar form as the Ya identifiers 35, 36.

Again, some of the identifiers Yb may be sufficient to define the disposition of the MUI 9 alone and thus propagate to the output stage 59 while others may become features for the third stage 50 identifier equations along with features pertinent to the Yb identifiers, all denoted as Xc. For the RDIS-10, a hybrid system combining inspection and data acquisition, depending on the constrains, those features can be obtained from data or functions entered by the operator 58, stored in historical data 57, or other predetermined sources (not illustrated). It should be understood that this process may repeat until an acceptable solution to the constrains is obtained, however, three stages are typically adequate for the exemplary STYLWAN RDIS-10, a hybrid system combining inspection and data acquisition, (STYLWAN is a trademark of Stylwan, Incorporated).

For the determination of the $a_{ik}$ coefficients, the tuning of the identifier equations, a set of flaw spectrums 1 of known similar imperfections that are pertinent to a current inspection application are required. These data sets, of flaw spectrums 1, are referred to herein as baseline spectrums. Preferably, all the $a_{ik}$ coefficients are initially set equal. It should be understood that because this is an iterative process the initial values of the a coefficients could also be set by a random number generator, by an educated guess, or by other means for value setting.

Since the baseline spectrums are well known, typically comprising data taken for similar imperfections, the performance measure and the constrains are clearly evident and the coefficients solution is therefore objective, although the selection of the imperfections may be subjective. By altering the coefficient values through an iterative process while monitoring the output error an acceptable solution would be obtained.

There are multiple well-known techniques to minimize the error and most of these techniques are well adept for computer use. It should be appreciated that for the autonomous NDI limited number of features a trial-and-error brute force solution is feasible with the available computer power. It should be further expected that different solutions would be obtained for every starting set of coefficients. Each solution is then evaluated across a variety of validation spectrum as each solution has its own unique characteristics. It is imperative, therefore, that an extensive library of both baseline spectrums and validation spectrums must be available for this evaluation. It should be further understood that the baseline spectrums cannot be used as validation spectrums and visa versa. Furthermore, it should be understood that more than one solution may be retained and used for redundancy, conflict resolution, and system stability. Still further in applications of the autonomous NDI, the terms "acceptable" or "good enough" are terms of art to indicate that, in a computational manner, the computer has completed an adequate number of iterations to compile an answer/solution with a high probability of accuracy.

Once a set or sets of coefficients are obtained, the number of non-zero coefficients is preferably minimized in order to improve computational efficiency. This is important because each identifier equation is just a subsystem and even minor inefficiencies at the subsystem level could significantly affect the overall system real time performance. Multiple techniques can be used to minimize the number of non-zero coefficients. A hard threshold would set all coefficients below a predetermined set point to zero (0). Computers typically have a calculation quota, so a quota threshold would set to zero a sufficient number of lower value coefficients to meet the calculation quota. A soft threshold would subtract a non-zero constant from all coefficients and replace the negative values with zero (0). Since an error measure exists, the new set of coefficients can be evaluated, the identifier equations can be tuned again and the process could repeat until the admissible identifier equation is determined. It is preferred that multiple admissible identifier equations are determined for further use. It should be appreciated that although the preference for multiple admissible identifiers may appear to complicate potential resolutions, the use of computer power makes a large number of iterations feasible.

For the inspection of materials, an acceptable solution would always contain statistics based on false-positive and false-negative ratios. A false-positive classification rejects good material while a false-negative classification accepts defective material. Using more than one identifier equation lowers the false ratios more than the fine-tuning of a single identifier equation. It should be understood that this process theoretically provides an infinite number of solutions, as an exact formulation of the inspection problem is elusive and always based on constrains. Furthermore, for a solution that can be obtained with a set of coefficients, yet another solution that meets the performance measure may also be obtained by slightly adjusting some of the coefficients. However, within the first three to five proper iterations the useful solutions become obvious and gains from additional iterations are mostly insignificant and hard to justify.

Once all of the Stage-I 30 admissible identifier equations have been determined, their identifiers become features in Stage-II 40 along with the additional features 41, bias 44, and forward and backwards chaining 49. The starting set of baseline spectrums is then processed through the admissible identifier equations and the results are used to tune the Stage-II 40 identifier equations in a substantially identical process as the one described above for the Stage-I 30. The process repeats for the Stage-III 50 identifier equations and any other stages (not illustrated) that may be desired or necessary until all the admissible subsystems are determined and the overall system design is completed. It should be appreciated that in practice, preferably only two to five stages will be necessary to obtain required results. When the final coefficients for all of the equations are established, the overall system performance may be improved by further simplifying the equations using standard mathematical techniques.

A previous inspection with the same equipment provides the best historical data 57. The previous inspection system output, denoted as $Ys_{(-1)}$, is ideally suited for use as a feature 51 in the current inspection as it was derived from substantially the same constrains. Furthermore, more than one previous inspection 57 may be utilized. Features 51 may be backwards chained 49, 39. Multiple historical values may allow for predictions of the future state of the material and/or the establishment of a service and maintenance plan.

In conventional inspection systems, previous state data, that was derived through a different means under different constrains, could not necessarily be used directly or used at all. If utilized, the data would more likely have to be translated to fit the constrains of the current application. It should be appreciated that such a task may be very tedious and provide comparatively little payoff. For example, there is no known process to translate an X-Ray film into MFL pertinent data. However, the system described herein allows for the use of such data in a simple and direct form. In the X-Ray example, the opinion of an X-Ray specialist may be solicited regarding the previous state of the material. The specialist may grade the previous state of the material in the range of one (1) to ten (10), with one (1) meaning undamaged new material. The X-Ray specialist opinion is an example of bias 34, 44, 54.

Bias 34, 44, 54 may not necessarily be derived in its entirety from the same source nor be fixed throughout the length of the material. For example, information from X-Rays may be used to establish the previous material status for the first 2,000 feet of an 11,000 foot coiled tubing string. Running-feet may be used to establish the previous material status for the remainder of the string except the 6,000 foot to 8,000 foot range where OD corrosion has been observed by the inspector 58. From the available information, the previous material status for this string (bias per 1,000 feet') may look like [2, 2, 4, 4, 4, 4, 7, 7, 4, 4, 4] based on length. Other constrains though may impose a hard threshold to reduce the bias into a single value, namely [7], for the entire string.

An example of a bias array would be a marine drilling riser string where each riser joint is assigned a bias based on its age, historical use, Kips, vortex induced vibration, operation in loop currents, visual inspection, and the like. The bias for a single riser joint may then look like [1, 1, 3, 1, 2, 2]. Identifier equations may also be used to reduce the bias array into a bias value or a threshold may reduce the bias into a single value.

The overall system must be feasible not only from the classification standpoint but also from the realization standpoint. In addition to the classification and minimum error, the system constrains also include, but are not limited to, cost, packaging, portability, reliability, and ease of use; all of which should be addressed in each step of the design. The system design preferably must assign initial resources to each level and should attempt to minimize or even eliminate resources whose overall contribution is negligible. This can be accomplished by converting certain features to bias and evaluating the resulting error.

Computer 10 preferably recognizes the imperfection by comparing the final array of identifiers 55, 56, 59 with a stored imperfection template database. Once an imperfection is recognized, computer 10 may verify the correctness of the recognition by further evaluating intermediate identifiers.

Occasionally, the imperfection recognition becomes unstable with the final array of identifiers toggling between two solutions on each iteration. For example, during the inspection of used production tubing, the recognition may bounce back and forth between a large crack or a small pit. Resolution of such instability may be achieved by utilizing intermediate identifiers, by utilizing the previous recognition value, or by always accepting the worst conclusion (typically referred to as pessimistic classification). However, autonomous NDI instability may also be the outcome of improper backwards chaining or even faulty constrains. Slight increase in the coefficients of the backwards chained features may produce an output oscillation thus rapidly locating the problem feature and/or coefficients.

A conflict arises when the final array of identifiers points into two or more different MUI 9 conditions with equal probability. Again, resolution of such conflict may be achieved by utilizing intermediate identifiers, by utilizing the previous recognition value or by always accepting the worst conclusion. However, a definite solution may be obtained by eliminating features that the conclusions have invalidated and by reprocessing the signals under the new rules.

The autonomous NDI is preferably designed to reason under certainty. However, it should also be capable of reasoning under uncertainty. For example, during the inspection of used production tubing of a gas well, rodwear is detected. Since there are no sucker rods in the gas well, the conclusion is that this is either used tubing that was previously utilized in a well with sucker rod or there is a failure in the autonomous NDI. The autonomous NDI could query 58 about the history of the tubing and specifically if it was new or used when initially installed in the well. The answer may be difficult to obtain, therefore a 50—50 chance should be accepted. A bias value may then be altered and the signal may be reprocessed under the new rules.

Alternate coefficients may be stored for use when certain failures are detected. For example, the wellhead pressure transmitter may fail. Upon detection of the failure, the alternate set of coefficients should be loaded for further use. It should be understood that even a simple bias may substitute for the failed transmitter.

Figure 3:
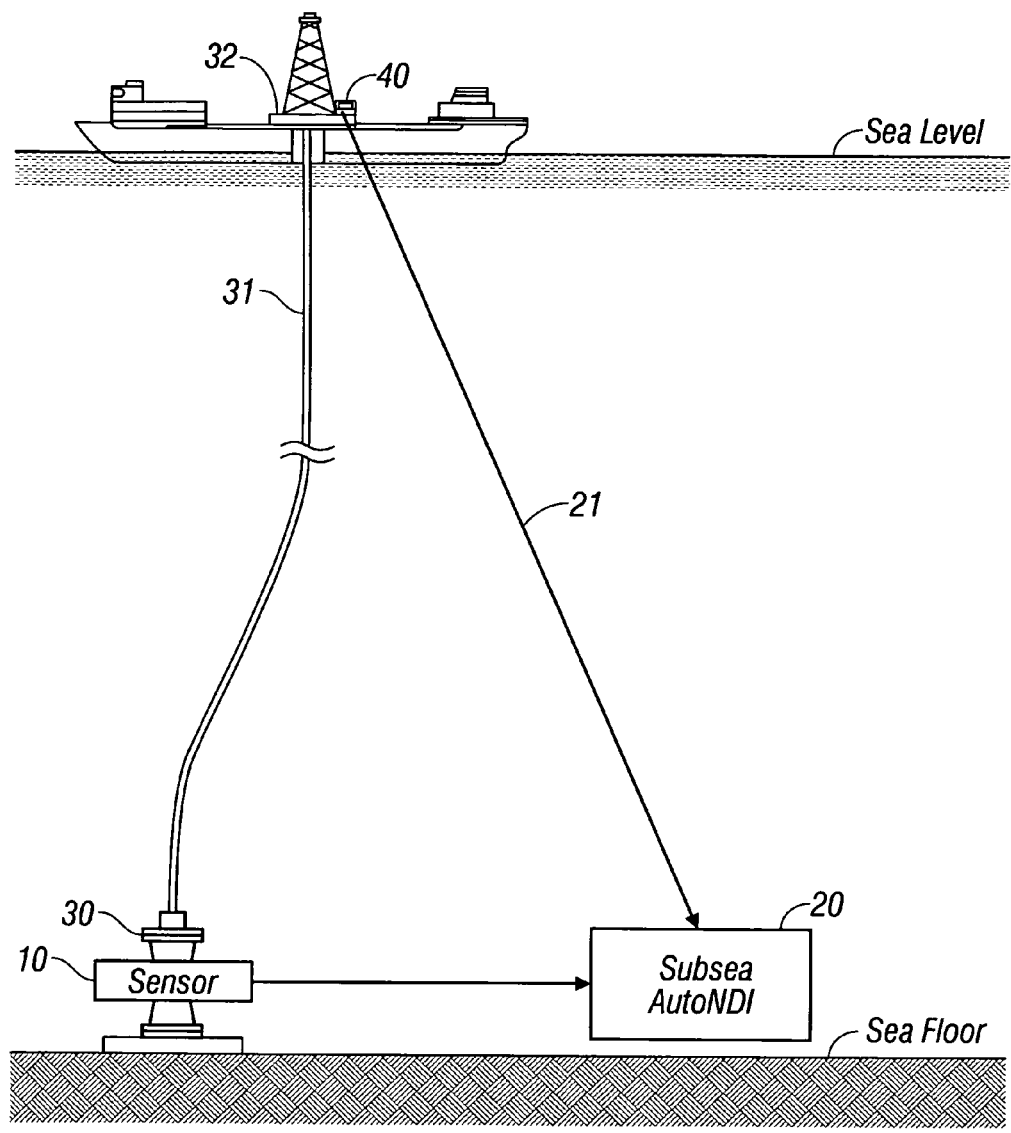
FIG. 3 illustrates a partially pictorial view using an autonomous non-destructive inspection system to locate well equipment according to the present invention.

As illustrated in FIG. 3 an autonomous NDI system can also be used to locate well equipment such as, but not limited to a tool joint. In offshore drilling there may be a need for an emergency disconnect between a drilling rig and the sea-floor wellhead. For example, due to inclement weather, a dynamically positioned rig may no longer be able to maintain its position above the sea-floor wellhead. Typically, such a disconnect is referred to as an Emergency Disconnect Sequence or EDS. A properly executed EDS allows the rig to move off location without damaging the subsea equipment and still maintaining control of the well.

A typical EDS mandates that the drill string is picked up and hung off in the subsea blow-out preventor ("BOP") pipe rams. The sequence typically starts by pulling some of the drill pipe out of the wellbore and then closing the BOP pipe rams on what it is estimated to be the center of a drill pipe joint. The drill string is then slacked off slowly until the tool joint lands on the shoulder of the closed BOP pipe rams. This is typically indicated by a drop in the weight indicator.

Thus, it becomes necessary to estimate the location of the tool joint in the subsea stack with a high degree of confidence otherwise the rubber goods of the BOP pipe rams may become damaged and significantly reduce their effectiveness to hold pressure. Knowing the exact location of the drill pipe tool joint in the subsea stack is critical information as it reduces the likelihood for damage to the BOP pipe rams and further assures that the shear rams will not close on a tool joint.

Due to the high operating pressures endured by the subsea stack, the drill pipe is typically surrounded by materials with a wall thickness in excess of one inch. Placing sensors inside the stack would appear to be the solution, however, this would expose the sensors to the action of the drilling fluids and the drill pipe, thus mandating armor around the sensors. Calculations would reveal that the armor would be of significant thickness itself and would require the redesign of subsea assemblies in order to accommodate the armored sensors and still maintain a desired 1D clearance within the bore of the subsea stack.

External sensors can be fitted on existing stack components with minimal or no alteration. However, the exciter (6 in FIG. 1) for the external sensors (7 in FIG. 1) would have to have sufficient power for the excitation to penetrate through the significant wall thickness in order to detect the drill pipe tool joint, thus, the detection system would require high power. Both space and power are extremely limited and of high value on the sea floor and on the subsea stack. Thus, the use of active tool joint detection techniques, such as, but not limited to, electromagnetic, ultrasonic, and radiation would be cost prohibitive.

The present invention overcomes these problems by utilizing a very low power passive tool joint detection technique that can be easily installed on new equipment as well as retrofitted on existing equipment. The locator requires an autonomous NDI 70 unit on the surface in communication with a subsea Autonomous NDI 20. When the drill pipe is tripped into the well, the surface autonomous NDI 70 prepares the drill pipe for both tool joint location and the subsequent inspection. When the drill pipe is tripped out of the well, the surface autonomous NDI 70 inspects the drill pipe and the subsea Autonomous NDI 20 locates the tool joints in the subsea stack. It should be understood that more than one subsea autonomous NDI 20 may be deployed in order to increase the overall system reliability and availability.

The drill pipe or tubular is magnetized at the rig floor while it is tripped into the well. At least one passive sensor 10, such as a coil, is preferably mounted externally on a convenient subsea stack component 30, thus the distance between the pipe rams and the tool joint sensor is fixed and known to the driller. It should be appreciated that a passive sensor may also be mounted internally to a subsea stack component. Active sensors, such as, but not limited to, hall probes, may also be used, placing a higher power requirement on the system. It should be further appreciated that the sensor 10 can also be any other autonomous NDI sensor. It should be further understood that more than one sensor configuration, each of which are known in the art, may be employed to increase the probability of the tool joint identification.

The subsea autonomous NDI 20 is preferably connected to the surface with two wires 21 for both power and communication. The surface autonomous NDI 70, is preferably located on the rig floor 32 of the drilling rig, drill ship or other drilling platform and would inform the driller when a tool joint is inside the sensor. The preference for a subsea autonomous NDI 20 is because of the distance between the sensor and the surface autonomous NDI 70. The typical applications for the tool joint locator are in water depths of more than three hundred feet (300').

The tool joint identification signature is a function of the drill pipe dimensions and the location of the tool joint sensor since different rigs use different drill pipe sizes and different subsea components. Thus, a training sequence would be required to tune the different identifier equations. The coefficients would preferably be stored onboard the subsea autonomous NDI 20 and be selected through the communication link 21. Since the entire function of the subsea autonomous NDI 20 is to detect a tool joint, preferably it would utilize a sufficient number of identifier equations to increase the probability of detection.

Figure 4:
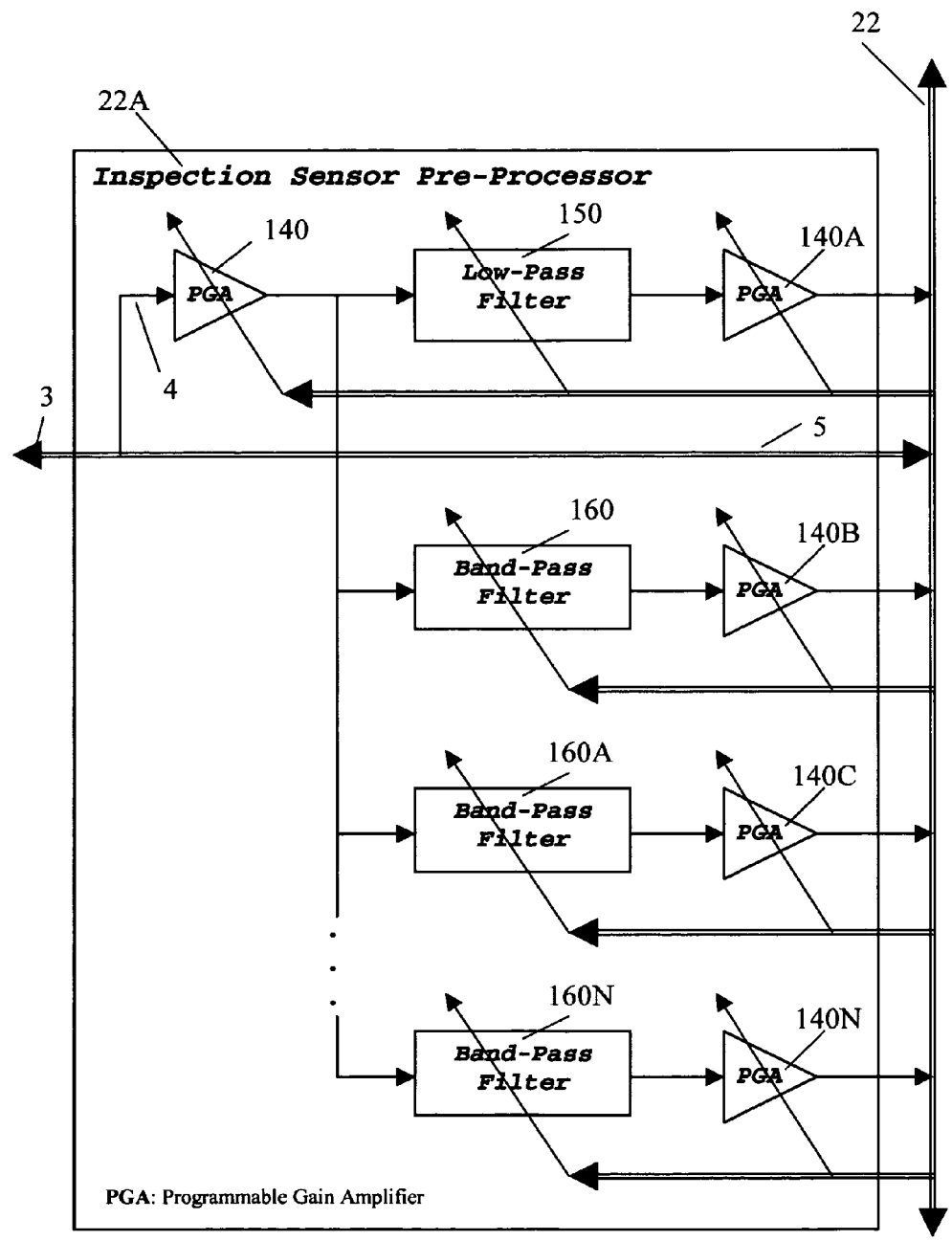
FIG. 4 illustrates a block-diagram of the imperfection sensor interface and the filter arrangement according to the present invention.
Figures 5A, 5B, 5C, 5D:
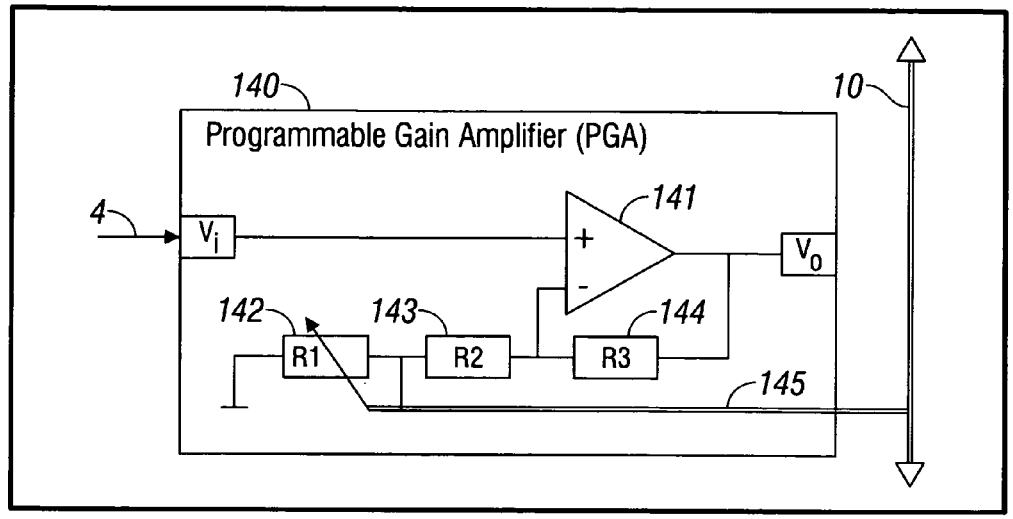
FIG. 5A illustrates a programmable gain amplifier according to the present invention.
FIG. 5B illustrates a mathematical formula for programing the programmable gain amplifier of FIG. 5A according to the present invention.
FIG. 5C illustrates an example of a mathematical formula for programing the programmable gain amplifier of FIG. 5A according to the present invention.
FIG. 5D illustrates an example of a mathematical formula for programing the programmable gain amplifier of FIG. 5A according to the present invention.

FIG. 4 illustrates a block-diagram of the modifications to the exemplary RDIS-10, a hybrid system combining inspection and data acquisition, imperfection sensor interface 22 (illustrated as preprocessor 22A to the sensor interface 22) and the filter arrangement to decompose the inspection signals frequency spectrum and extract relevant features in an analog format. The features extraction of the present invention is accomplished through a filter bank comprising of a low-pass filter 150 and a number of band-pass filters 160, 160A through 160N. There is no limit on the number of band-pass filters that may be used, however six to eight filters are adequate for most applications thus dividing the sensor frequency spectrum into seven to nine features, the exact number depending on the specific application. It should be understood that the amplifiers and the filter bank of FIG. 4 comprise a modification to the front end of the inspection sensor interface 22 of the exemplary RDIS-10, a hybrid system combining inspection and data acquisition, in order to retrofit the present invention to existing MFL inspection units. For a scanning speed of 60 feet/minute a typical alignment time shift (also known as time delay) is 42 milliseconds and a typical nine filter sequence comprises one 12 Hz low-pass filter 150 and eight band-pass filters 160, 160A through 160N with center frequency (bandwidth) of 15 Hz (6 Hz), 25 Hz (10 Hz), 35 Hz (15 Hz), 50 HZ(21 Hz), 70 Hz(30 Hz), 100 Hz(42 Hz), 140 Hz(58 Hz) and 200 Hz(82 Hz). The attenuation of the filters depends on the resolution of the analog-to-digital converter and the processing with 40 to 60 decibels been sufficient for common applications. The passband ripple is another important filter consideration. In the past, the NDI industry has mostly used Butterworth (also known as maximally-flat) filters. These are compromise filters with a 3 db passband variation. For typical NDI applications, better performance is achieved with Chebyshev or Elliptic filters. For example, a 0.5 db Chebyshev filter has less passband variation and sharper rolloff, thus resulting in a lower order filter than an equivalent Butterworth. The above specifications (filter type, center frequency, bandwidth and attenuation) are sufficient to design the filters without additional experimentation. Filter design software, some available free of charge, is also available from multiple component vendors such as, Micro-Chip, Linear Technology, and many others.

Preferably, the computer 10 may read and gather relevant sensor 5 information from the sensor 7 onboard memory and may write new information into the sensor 7 onboard memory. It should be understood that the sensor 7 relevant information may also be stored in other storage media, such as hard disks, floppy disks, compact discs, magnetic tapes, DVDs, memory, and other storage devices that computer 10 may access. The sensor 7 analog signal 4 is amplified by a programmable gain amplifier (herein after referred to as "PGA") 140. This Gain of the PGA 140 is controlled by the computer 10. FIGS. 5A–5D illustrates a PGA and its design equations for clarity. PGAs are well known in the art and multiple designs can be found throughout the literature. PGA integrated circuits are also commercially available from such vendors as Analog Devices, Linear Technology, Maxim, National Semiconductors, Texas Instruments, and many others. In its simplest form a PGA comprises a differential amplifier 141 with a variable resistor 142 inserted in its feedback loop. Preferably, the variable resistor 142 is a digitally controlled potentiometer such as the ones offered by XICOR. Computer 10 may vary the variable resistor 142 value thus adjusting the gain of the PGA 140. The PGA 140 gain adjustment is primarily controlled by the sensor information 5, the instantaneous scanning speed derived by the computer 10 from sensor 24 and the specific MUI 9. The output of PGA 140 is connected to a filter bank in order to decompose the inspection signals frequency spectrum and extract relevant features.

Figures 6A, 6B, 6C:
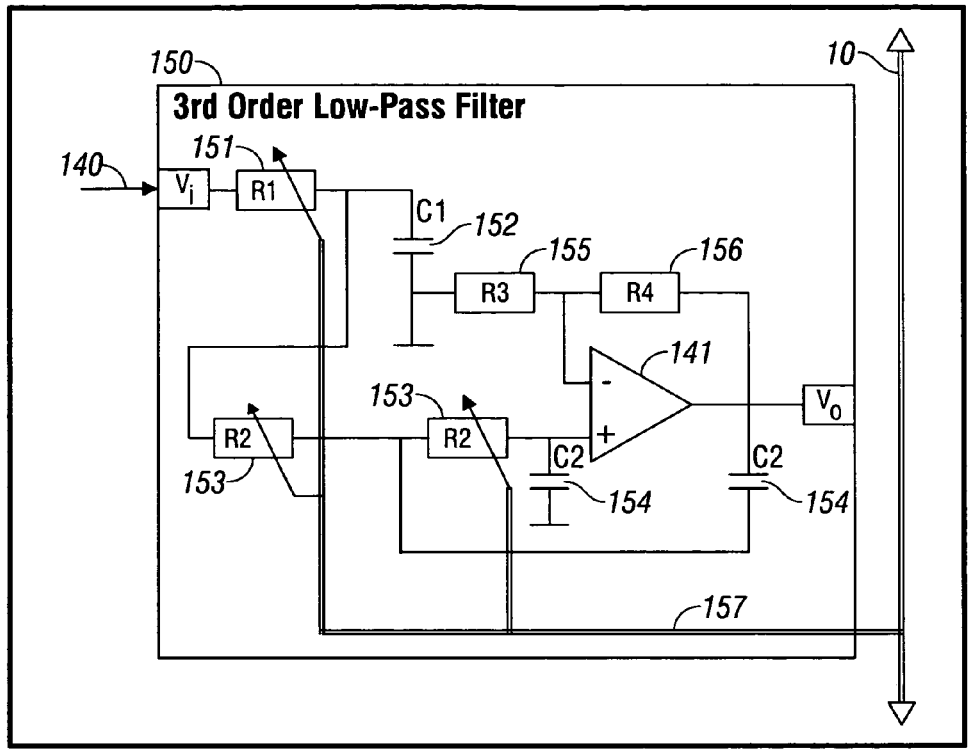
FIG. 6A illustrates a programmable $3^{rd}$ order low-pass filter according to the present invention.
FIG. 6B illustrates a mathematical formula for $1^{st}$ order low pass filters of FIG. 6A according to the present invention.
FIG. 6C illustrates a mathematical formula for $2^{nd}$ order low pass filters of FIG. 6A according to the present invention.

The low frequency components are extracted by the low-pass filter 150. It should be understood that the term low-frequency features are not in absolute terms but in relative terms to the scanning speed. Therefore, the cutoff frequency of the low-pass filter 150 , denoted as Fc in FIGS. 6A–6C, may be set to 5 Hz for one scanning speed and to 50 Hz for a higher scanning speed. The exact cutoff frequency of the low-pass filter 150 depends on the sensor information 5, the instantaneous scanning speed derived by the computer 10 from sensor 24, and the specific MUI 9. FIGS. 6A–6C illustrates a programmable $3^{rd}$ order low-pass analog filter and its design equations for clarity. Low-pass filters are well known in the art and their design can be found throughout the literature. Filter design software, some available free of charge, is also available from multiple component vendors such as, MicroChip, Linear Technology, and many others. The low-pass filter of FIGS. 6A–6C includes of two sections. A $1^{st}$ order filter comprising of resistor 151 and capacitor 152 cascaded with a $2^{nd}$ order low-pass analog filter. It should be understood that all other filter orders can be obtained by cascading additional filter sections. Preferably, the variable resistors 151 and 153 are digitally controlled potentiometers such as the ones offered by XICOR and a fixed resistor value (not shown) similar to the FIGS. 5A–5D network 142 and 143. Computer 10 may vary the variable resistor 151 and 153 value thus adjusting the cutoff frequency of the low-pass filter.

Figures 7A, 7B, 7C:
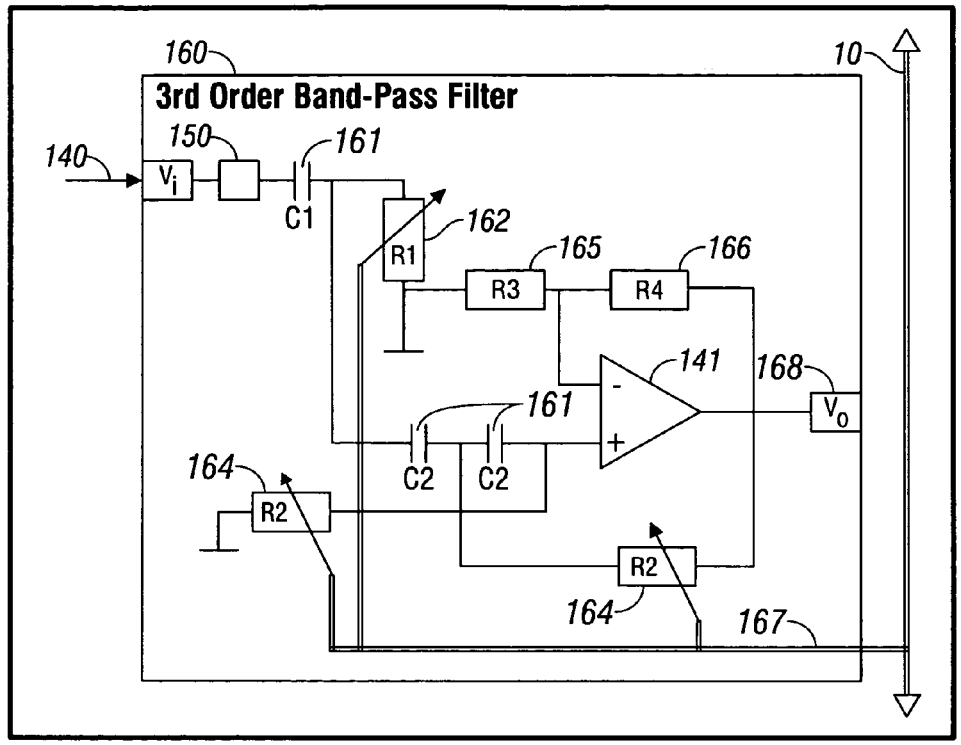
FIG. 7A illustrates a programmable band-pass filter according to the present invention.
FIG. 7B illustrates a mathematical formula for $1^{st}$ order low pass filters of FIG. 7A according to the present invention.
FIG. 7C illustrates a mathematical formula for $2^{nd}$ order low pass filters of FIG. 7A according to the present invention.

All other frequency components of the sensor signal 4 are extracted by the band-pass filters 160, 160A through 160N. Again, it should be understood that the frequency bands are not stated in absolute terms but in relative terms to the scanning speed. Therefore, the center frequency of a band-pass filter 160, 160A through 160N may be set to 40 Hz for one scanning speed and to 200 Hz for a higher scanning speed. The exact center frequency of the band-pass filters 160, 160A through 160N depends on the sensor information 5, the instantaneous scanning speed derived by the computer 10 from sensor 24 and the specific MUI 9. FIGS. 7A–7C illustrates a programmable $3^{rd}$ order band-pass filter that is made up from a low-pass filter 150 cascaded with a $3^{rd}$ order high-pass filter. The $3^{rd}$ order high-pass filter and its design equations are shown for clarity. High-pass filters are well known in the art and its design can be found throughout the literature. Filter design software, some available free of charge, is also available from multiple component vendors such as, MicroChip, Linear Technology, and many others. The high-pass filter of FIGS. 7A–7C includes two sections. A $1^{st}$ order filter comprising of capacitor 161 and resistor 162 cascaded with a $2^{nd}$ order high-pass filter. It should be understood that all other filter orders can be obtained by cascading additional filter sections. Preferably, the variable resistors 162 and 164 are digitally controlled potentiometers such as the ones offered by XICOR and a fixed resistor value (not shown) similar to the FIGS. 5A–5D network 142 and 143 Computer 10 may vary the variable resistor 162 and 164 value thus adjusting the cutoff frequency of the high-pass filter. It should be further understood that the this band-pass filter configuration allows for individual adjustment of both the leading and trailing transition bands. Other band-pass filter configurations can also be found throughout the literature.

Figure 8:
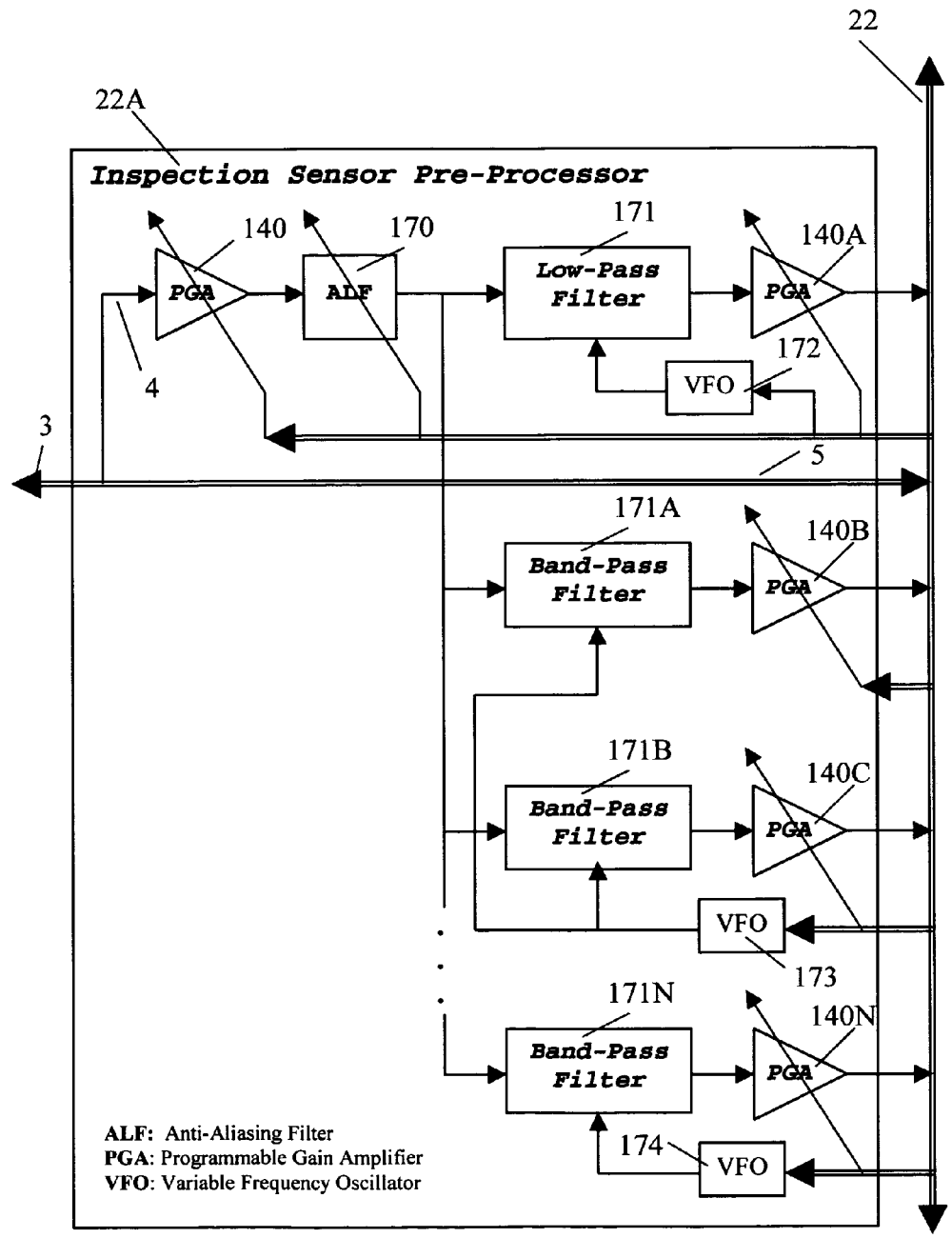
FIG. 8 illustrates a block-diagram of the imperfection sensor interface and the switched capacitor filter arrangement according to the present invention.

Although the features extraction filter bank has been described above using analog filters, equal performance can be achieved by using switched capacitor filters as shown in FIG. 8 where an anti-aliasing filter 170 follows PGA 140. It should be understood that the amplifiers and the filter bank of FIG.8 comprise a modification to the front end of the inspection sensor interface 22 (i.e. preprocessor 22A) of the exemplary RDIS-10, a hybrid system combining inspection and data acquisition, in order to retrofit the present invention to existing MFL inspection units. Switched capacitor filters are offered by semiconductor manufacturers such as Linear Technology, National Semiconductors, and others along with software, some free of charge, to design such filters. An advantage of switched capacitor filters enjoy is that their pass band is controlled by the frequency of the switching clock in a typical 50 or 100 ratio. Computer 10 slides the features extraction filter bank based on the scanning speed detected by sensor 24 by adjusting the frequency of the Variable Frequency Oscillators (herein after referred to as "VFO") 172, 173, 174. It should be understood that each filter may utilize its own VFO, such as 171, 172 and 171N, 174, or a single VFO may control more than one filter, such as 171A, 171B and 173. The output of each filter is followed by a reconstruction filter and a PGA (140A through 140N). The reconstruction filter can be a low-pass filter such as the ones shown in FIGS. 6A–6C.

The features extraction filter bank that was described above using analog or switched capacitor filters can also be implemented using digital filters and/or mathematical transform in the digital domain. It should be understood that no modification to the front end of the inspection sensor interface 22 (i.e. no preprocessor 22A as described hereinabove) of the exemplary RDIS-10, a hybrid system combining inspection and data acquisition, is required in order to implement the present invention using digital filters and/or mathematical transforms as the exemplary RDIS-10, a hybrid system combining inspection and data acquisition, is designed for digital domain operation.

The sensor signal therefore, is converted to digital format and the analog filters described above may be converted to their digital counterpart using bilinear transform which is well known to the art and well publicized resulting in Infinite Impulse Response digital filters (known to the art as IIR filters) and is illustrated in FIGS. 9A–9D. The block diagram of FIG. 4 or FIG. 8 may then be used to derive the flowchart of the digital signal processing form of the present invention. In another implementation, digital filters may be designed using direct synthesis techniques that are also well known to the art and well publicized. Finite Impulse Response digital filters (known to the art as FIR filters) may also be employed at the expense of computing power. FIR implementations, such as Kaiser, Hamming, Hanning etc, are also well known to the art and well publicized.

There are many mathematical transforms that are well known and well publicized. However, not all are useful for features extraction for the transient NDI signals. The NDI industry in the past has proposed the use of Fourier Transform or its Fast Fourier Transform (FFT) implementation, a misapplication for the brief transient NDI imperfection signals. Fourier Transform, in all of its implementations, is useful to analyze long periodic signals (long waves). Furthermore, the Fourier Transform provides information in the frequency domain and none in the time domain which is essential for the analysis of NDI signals. This drawback of the Fourier Transform was noted by the French Academy and in particular by J. L. Lagrange who objected to the Fourier Transform trigonometric series because it could not represent signals with corners such as the ones often encountered in NDI. Subsequently, the Academy refused to publish the Fourier paper. In order to overcome the drawbacks of the Fourier Transform, alternatives were developed over the years, notably the Short Time Fourier Transform (commonly referred to as STFT), wavelets and coiflets all of which are well known to the art and well publicized. The main disadvantages of the transforms are their fixed resolution and their demand for higher computer power.

The STFT offers uniform time and frequency resolution throughout the entire time-frequency domain using a fixed window size, which results in its main drawback. A small window blind the STFT to low frequencies while a large window blinds the STFT to brief signal changes mostly associated with use induced MUI 9 imperfections. Wavelets (short waves) are better tuned to the needs of NDI. Wavelets vary the width of the window thus offer better time resolution for the higher frequencies that are typically associated with use induced MUI 9 imperfections. Wavelets are typically implemented using filter banks and they are also well known in the art and well publicized. FIGS. 10A–10C illustrates the implementation of the discrete wavelet transform decompostion using filter banks.

FIGS. 4 and 8 illustrate a bank of PGAs 140A through 140N following the features extraction filter bank. The frequency response of the inspection sensors 7 is typically non-linear. The response of the inspection sensor 7 to the same MUI 9 imperfection would then vary depending on the scanning speed and level of excitation which is continuously monitored by computer 10. The sensor 7 response to different scanning speeds, in the unique setting of the inspection head 8 under varying excitation 21 levels, can be characterized. This is accomplished by scanning MUI 9 samples with test imperfections at different speeds and different levels of excitation while recording the sensor 7 signals. Preferably, these sensor characterization tests would be repeated multiple times so that a sufficiently large database for the specific sensor is obtained. The characteristics of the particular sensor 7 are then preferably stored in the memory onboard the sensor 7. Computer 10 reads the sensor characteristics 5 and adjusts the bank of PGAs 140A through 140N to compensate the signal amplitude. This band signal amplitude compensation along with the capability of computer 10 to adjust both the pass-band width and the transition slopes of the filters in FIGS. 6 and 7 allows computer 10 to fully compensate the imperfection signals.

The outputs of the bank of PGAs 140A through 140N are then converted to digital form through an analog-to-digital converter of sufficient resolution, typically 10 to 12 bits, and speed which is defined by the number of channels and maximum scanning speed.

It may be seen from the preceding description that a novel autonomous inspection system and control has been provided including through spectral analysis. Although specific examples may have been described and disclosed, the invention of the instant application is considered to comprise and is intended to comprise any equivalent structure and may be constructed in many different ways to function and operate in the general manner as explained hereinbefore. Accordingly, it is noted that the embodiments described herein in detail for exemplary purposes are of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. An inspection system to detect imperfections in materials comprising:

at least one imperfection detection sensor with an output, said output comprising imperfection signals in a time-varying electrical form;

at least one computer having at least one imperfection detection interface, wherein said output is normalized and decomposed in frequency and is in communication with said at least one computer, and wherein said at least one computer converts the frequency decomposed imperfection signals to a digital format;

at least one memory storage for said at least one computer, wherein said output can be stored; and a program, said program being executed on said at least one computer, and said program being configured to operate on said converted frequency decomposed imperfection signals, wherein said operation evaluates and/or manages said converted frequency decomposed imperfection signals, wherein said conversion to digital format further comprises at least one sampling rate, and wherein the at least one sampling rate of said conversion to digital format is at least partially controlled by a scanning speed of the inspection system.

2. The inspection system of claim 1, further comprising the induction of an excitation into a material and detecting the response to the excitation through said at least one imperfection detection sensor.

3. The inspection system of claim 2, wherein said excitation is controlled by said at least one computer.

4. The inspection system of claim 1, wherein said at least one imperfection detection sensor further comprises memory storage, and wherein processing coefficients and/or processing rules can be stored and accessed by said at least one computer.

5. The inspection system of claim 4, wherein said at least one imperfection detection sensor further comprises at least one frequency response characteristic, and wherein the at least one frequency response characteristic is at least partially stored in the memory storage of said at least one imperfection detection sensor.

6. The inspection system of claim 5, wherein said at least one imperfection detection sensor further comprises at least one type of imperfection response characteristic, and wherein the at least one type of imperfection response characteristic is at least partially stored in the memory storage of said at least one imperfection detection sensor.

7. The inspection system of claim 4, wherein said at least one imperfection detection sensor further comprises at least one excitation response characteristic, and wherein the at least one excitation response characteristic is at least partially stored in the memory storage of said at least one imperfection detection sensor.

8. The inspection system of claim 1, wherein said normalization of said output further comprises adjustments for an amplitude, and/or a phase, and/or a time shifting, and/or a scanning speed, and/or for response characteristics of said at least one imperfection detection sensor.

9. The inspection system of claim 1, wherein a filter bank performs said frequency decomposition.

10. The inspection system of claim 9, wherein said filter bank comprises at least one low-pass filter, and/or at least one high-pass filter, and/or at least one band-pass filter, and/or at least one band-reject filter.

11. The inspection system of claim 10, wherein the filter bank is realized in analog or digital form.

12. The inspection system of claim 1, wherein said frequency decomposition is performed by a mathematical transform in the digital domain.

13. The inspection system of claim 12, wherein said mathematical transform in the digital domain comprise short-time Fourier transform, and/or wavelets, and/or coiflets.

14. The inspection system of claim 1, further comprising historical data, wherein said historical data is compiled from a prior analogous and/or a non analogous inspection technique, and where said historical data is inputted into said at least one computer to manage and evaluate the imperfection signals.

* * * * *